(12) United States Patent
Kanner et al.

(10) Patent No.: US 7,495,823 B2
(45) Date of Patent: Feb. 24, 2009

(54) OPTICAL METHOD AND SYSTEM FOR ANALYZING OR INSPECTING PATTERNED MATERIALS

(75) Inventors: Gary Stewart Kanner, Algonquin, IL (US); Michael L. Marable, Crystal Lake, IL (US)

(73) Assignee: Northrop Grumman Corporation, Los Angeles, CA (US)

( * ) Notice: Subject to any disclaimer, the term of this patent is extended or adjusted under 35 U.S.C. 154(b) by 0 days.

(21) Appl. No.: 11/510,245

(22) Filed: Aug. 25, 2006

(65) Prior Publication Data

US 2008/0049300 A1    Feb. 28, 2008

(51) Int. Cl.
    *G02F 1/35*    (2006.01)
(52) U.S. Cl. ....................... 359/326; 359/325
(58) Field of Classification Search .............. 359/325, 359/326
    See application file for complete search history.

(56) References Cited

U.S. PATENT DOCUMENTS 5,061,041 A * 10/1991 Fergason ................... 349/7
2007/0140423 A1* 6/2007 Foland ..................... 378/57

FOREIGN PATENT DOCUMENTS

JP          63063004 A *  3/1988

* cited by examiner

*Primary Examiner*—Jennifer Doan
(74) *Attorney, Agent, or Firm*—Tarolli, Sundheim, Covell & Tummino LLP (57) ABSTRACT

A method to determine at least one characteristic of a material having a spatially modulated nonlinear susceptibility includes measuring scattered light in response to an incident beam provided to at least one surface of the material. An indication of patterning of the material is determined based on the measured scattered light.

20 Claims, 4 Drawing Sheets

OPTICAL METHOD AND SYSTEM FOR ANALYZING OR INSPECTING PATTERNED MATERIALS

BACKGROUND

Quasi-phasematching (QPM) employs a material with spatially modulated nonlinear properties. Compared with an ideal phasematched case (e.g., involving birefringent phase matching—BPM), QPM typically exhibits a lower conversion efficiency if the nonlinear coefficient is the same. However, QPM allows frequency conversion in isotropic materials or ones that exhibit little birefringence, and in some cases allows access to larger components of the nonlinear susceptibility tensor, with coupling of waves of the same polarization. QPM also has an advantage of eliminating spatial walkoff due to birefringence, enabling a greater degree of collinearity among output beams, and allowing use of longer crystals to obtain higher optical output powers. In effect, the conversion efficiency for QPM can be higher than that due to BPM.

Various techniques have been developed to engineer quasi-phasematching (QPM) in non-linear materials. For instance, periodic poling is a technique for obtaining quasi-phase matching of nonlinear interactions. Periodic poling involves a process (e.g., ferroelectric domain engineering) that generates a periodic reversal of the domain orientation in a nonlinear crystal, so that the sign of the nonlinear coefficient also changes. Another related approach can achieve ferroelectric domain reversals via thermal poling. A technique for engineering quasi-phase matching in non-ferroelectric crystals is semiconductor orientation-patterning. This technique allows frequency conversion to wavelengths well into the mid-infrared and even far infrared regime. Before these and other QPM materials can be utilized, it is desirable to verify that a modulation of the crystalline orientation has been achieved.

Although X-ray diffraction may seem like an obvious tool for inspection, the electron beams that are used are typically orders of magnitude larger (~mm) than many domain widths. Additionally, typical X-ray diffraction cannot distinguish between domains of inverted orientation in any case. Thus, the conventional scheme for characterizing orientation patterning of semiconducting crystals usually involves cleaving the device along the grating direction. An anisotropic etchant is then applied to the surface, and scanning electron micrography (SEM) or optical microscopy is employed to detect variations in sidewall profiles. This technique can be destructive, risking catastrophic damage to the samples, and requires knowledge of the appropriate etchant for attacking different orientations of the particular semiconductor at different rates.

SUMMARY

The present invention relates generally to a method and system for analyzing patterned materials.

One aspect of the present invention provides a method to determine at least one characteristic of a material having a spatially modulated nonlinear susceptibility. The method includes measuring scattered light in response to an incident beam provided to at least one surface of the material. An indication of patterning of the material is determined based on the measured scattered light. For example, the indication of patterning can be determined from an intensity of inelastically scattered light and/or intensity of phonons ascertained from the measured scattered light.

Another aspect of the present invention provides a system to determine a characteristic of a nonlinear crystalline material. The system includes means for determining a modulation in intensity of phonons in scattered light from the material. The system also includes means for determining an indication of patterning of the material based on the determined modulation in phonon intensity.

Yet another aspect of the present invention provides a system to analyze a material. The system includes a light source that provides an incident beam having a predetermined polarization and a predetermined frequency. A detection system is configured to detect scattered light from at least two adjacent domains of the material in response to the incident beam impinging on the at least two adjacent domains. A computer is programmed to determine an indication of patterning for the material based on the detected scattered light.

DETAILED DESCRIPTION

The present invention relates generally to systems and methods that can be utilized to determine characteristics of materials having spatially modulated non-linear properties, such as crystals. The approach described herein generally determines an indication of patterning of a material based on the detected intensity of light scattered by phonons in the material. As used herein, the term "patterning" is intended to encompass various types of spatially modulated nonlinear properties of a material. For example, such spatially modulated nonlinear properties can arise from a spatially modulated atomic orientation of the material (e.g., crystal orientation) or to a spatially modulated polarization of the material. Alternatively or additionally, patterning can be provided by utilizing different crystal structures or by having alternating domains of crystalline and amorphous structures. Such patterning of materials can be utilized to implement frequency conversion through quasi-phased matching (QPM), in which the second order nonlinear optical susceptibility of the material is spatially modulated.

The approach described herein can be considered nondestructive since the properties of the material being analyzed are not altered by the process. The approach is applicable to various types of quasi-phase matched materials, including films, waveguides, optical fibers, bulk crystals and other nonlinear materials. Those skilled in the art will understand and appreciate that the approach described herein is equally applicable to materials independent of the type of patterning and the way in which different types of materials can be engineered (e.g., via domain inversion).

Figure 1:
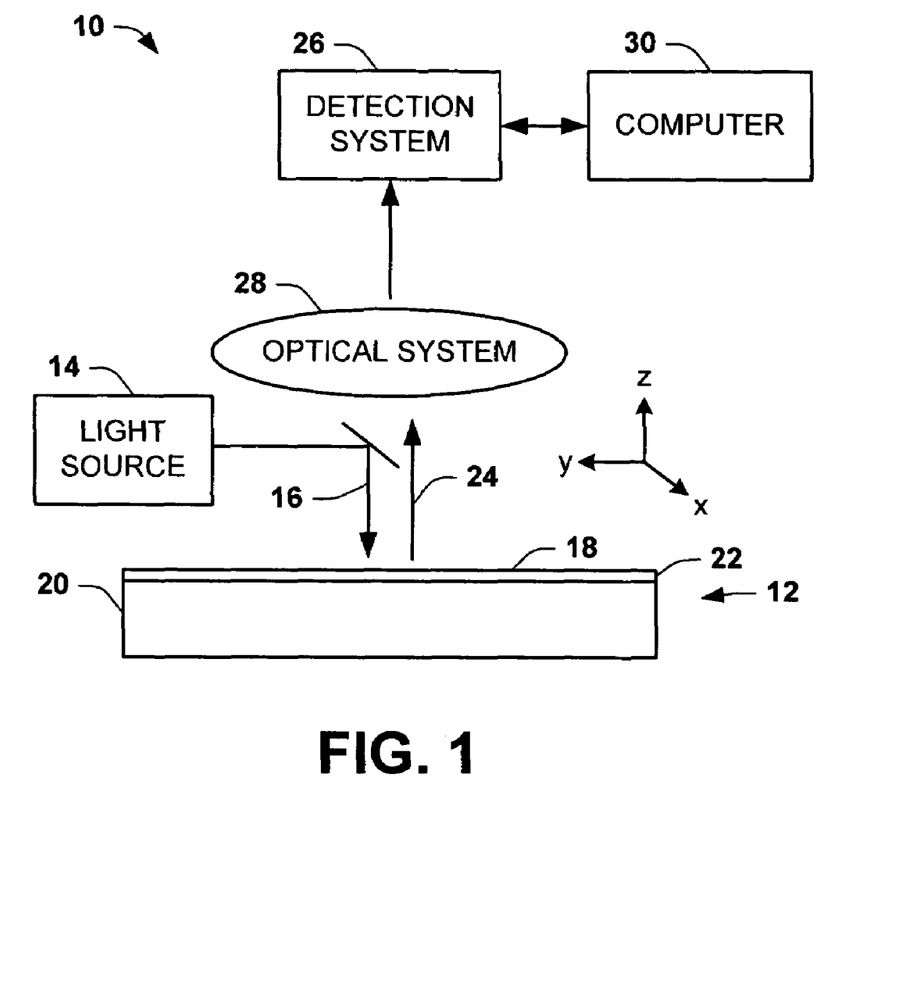
FIG. 1 depicts one example of a system to ascertain an indication of patterning of a non-linear material in accordance with an aspect of the present invention.

FIG. 1 depicts an example of a system 10 that can be utilized to analyze characteristics of a material 12 having spatially modulated nonlinear properties. For example, the system 10 can employ polarized Raman spectroscopy to determine (or verify) the patterning of the material 12. Those skilled in the art will understand and appreciate various types of systems and setups that can be utilized to collect information that can be utilized to determine characteristics of the orientation-patterned materials 12 according to an aspect of the present invention.

The system 10 includes a light source 14 that provides an incident light beam 16 that impinges on the material 12. The incident light beam 16 can be provided as a linearly polarized beam having a predetermined polarization and frequency (or wavelength). The predetermined polarization can be fixed or it can vary between different known polarization directions. The incident beam 16, for example, is provided with a frequency that is in resonance with an electronic transition of the material 12 that is under inspection. The incident beam 16 can also have a beam width or a spot size that impinges on the material 12 (e.g., at the surface 18) that is less than the width of the given domains. Those skilled in the art will appreciate various types of light sources (e.g., lasers) that can be utilized. The incident beam 16 can be scanned across the surface of the material 12 so as to impinge on adjacent domains. In this way, the scattered light from each of the adjacent domains exhibits a modulation in scattered light intensity according to the relative Raman susceptibility of each domain, and the light polarization configuration employed.

As used herein, the term "domain" is utilized to refer to a given region of the material 12 having a particular nonlinear susceptibility (e.g., second order nonlinear susceptibility). For example, in an orientation-patterned crystal material, the orientation of adjacent domains can be inverted with respect to each other relative to a given crystal axis. Such inversion along a given axis is referred to herein as a reversal (or inversion) of domain orientation. As is known in the art, a reversal or other modification of domain orientation along a given axis of the material 12 can be engineered from an electrically induced change in crystal polarization (e.g., by periodic poling) or by a modulation of orientation of the crystal along the light propagation path via epitaxial film growth. For purposes of simplicity of explanation, and not by way of limitation, several examples are described in the context of the material being an orientation-patterned crystal film. For example, the material 12 can include a substrate material (e.g., GaAs) 20 and an orientation-patterned film (e.g., ZnSe) 22 formed on the substrate. Such films 22 can be formed with a spatially modulated pattern of domains by epitaxial film growth (e.g., by molecular beam epitaxy, metalorganic chemical or physical vapor deposition).

The incident light beam 16 is scattered from the sample material 12, as backscattered light indicated at 24, and provided to a detection system 26 through an optical system 28. While the schematic example of FIG. 1 depicts a single arrow for the scattered light 24, corresponding to backscattered light, it will be appreciated that such scattering occurs in all directions, and, therefore, various detection geometries are possible with accordingly different selection rules. As mentioned above, the incident beam 16 should be provided at a frequency (or wavelength) that is in resonance with the electronic transition of the material 12 to enable adequate detection of the backscattered light 24 due to Raman scattering. For example, the incident light beam 16 can be provided to coincide with the maxima in the absorption spectrum, corresponding to the $E_0$ or $E_1$ transitions of the material 12.

The detection system 26 detects the scattered light from the optical system 28. The optical system 28 can include an arrangement of one or more lenses, filters, reflectors, polarizers and the like configured and arranged to process the backscattered light 24 and provide processed light to the detection system 26. For example, the detection system 26 can include a spectrometer or other spectroscopy apparatus that is configured to measure the spectrum of radiation in a particular wavenumber region corresponding to the scattered light 24. The polarization components of the scattered light 24 depend on the orientation of the axes of the material with respect to the plane of polarization of the input beam 16, as well as on the relative polarization of the input beam 16 and the observing polarizer, such as may be implemented in the optical system 28. The spectrometer response can be calibrated to enable a determination of the frequencies of the Raman-active excitations as well as the relative magnitudes of the scattering at different frequencies.

The detection system 26 can also include an array detector (e.g., a multi channeled charge-coupled device (CCD)) array. The spectrometer can focus the final dispersed image of the sample spot in the plane of the CCD array. The spectrometer can also filter out the frequency of the input beam 16, while leaving the rest of the frequencies unaffected, such that the filtered light is spread onto the CCD array. The CCD array responds uniformly to each frequency in the filtered light provided by the spectrometer providing a corresponding signal indicative of the Raman spectrum in the scattered light 24.

A computer 30 reads the wavelength and intensity information from the detection system 26 and employs software to convert such information to frequency and intensity information, such as corresponding to the Raman spectrum of the scattered light 24. It will be appreciated that this approach is not limited to a Raman spectrum (of optical phonons) as the frequency and intensity information can correspond to other types of inelastic scattering associated with a variety of vibrational, electronic, and magnetic excitations. As an example, the computer 30 can be programmed with executable instructions to determine an indication of patterning of the material 12 based on an intensity of light, such as an intensity of phonons, in the scattered light 24 received by the detection system 26. The computer 30 can be implemented as a personal computer, workstation or other equipment that is programmed and/or configured with executable instructions to implement the methods based on the teachings contained herein. The computer 30 can be a standalone machine or it may operate in a networked environment and/or in a distributed computing environment.

Because the incident beam 16 is provided to scan across the material 12 so as to impinge on the respective domains, the computer 30 can be programmed to determine an indication of patterning of the material 12 based on an intensity of phonons ascertained from the scattered light. For example, domains with alternating orientations along a given axis can exhibit different modulations of intensity for one or more types of phonons consistent with phonon selection rules for the material 12. The selection rules utilized can be specific to the surface on which the incident light impinges, the polarization configuration, and the type of detection being utilized. Accordingly, the computer 30 can discriminate between adjacent domains based on a modulation of intensity for one or more types of phonons based on which the patterning frequency can be determined. For example, the computer 30 can determine the indication of patterning (e.g., the grating period) by calculating the frequency at which the intensity of one or more types of phonons modulate.

As an example, the computer 30 can be preprogrammed with a set of known Raman tensors and phonon selection rules according to the type of material or materials 12 being inspected. A subset of such phonon selection rules can be utilized to determine the indication of patterning according to the expected orientation of the respective domains. For example, for a given material and a given Raman tensor for such material, appropriate selection rules can be employed to identify expected longitudinal optical phonons and transverse optical phonons for a given domain. As used herein, the term "selection rule" corresponds to a shorthand notation for the set of conditions under which a given transition matrix element is nonzero for a given phonon. Thus, the selection rules for Raman scattering for a given material 12 can be employed to identify conditions that will achieve a modulation in phonon intensity (e.g., for one or more type of phonon), based on which an indication of patterning can be determined by the computer 30.

Additionally, the Raman selection rules and Raman tensors can be adjusted to characterize one or more known symmetry-breaking effects associated with the material 12. As described in greater detail herein, the symmetry-breaking effects in materials can include, for example, substrate misorientation, Fröhlic interaction, surface field induced scattering, second ordering scattering (e.g., due to Brillouin scattering). The Raman tensors and Raman selection rules for a given material can be determined a priori or be obtained from various textbooks and other resources in advance to program the computer accordingly. Alternatively, techniques, which may be known or yet to be developed, can be implemented to derive the Raman tensors and selection rules for a given material as part of an inspection process.

Thus for a given material 12, having a known Raman tensor and for a given orientation of the crystal, the scattered light, upon scanning across the patterned domains, should exhibit peaks in the power spectral density (PSD) of a frequency domain representation that correspond to intensities of different types of phonons consistent with the selection rules for the given material. The computer 30 thus can be programmed to determine the modulation in intensity of phonons (e.g., LO, TO or a combination of LO and TO) and determine the patterning of the material according to appropriate selection rules.

Figure 2:
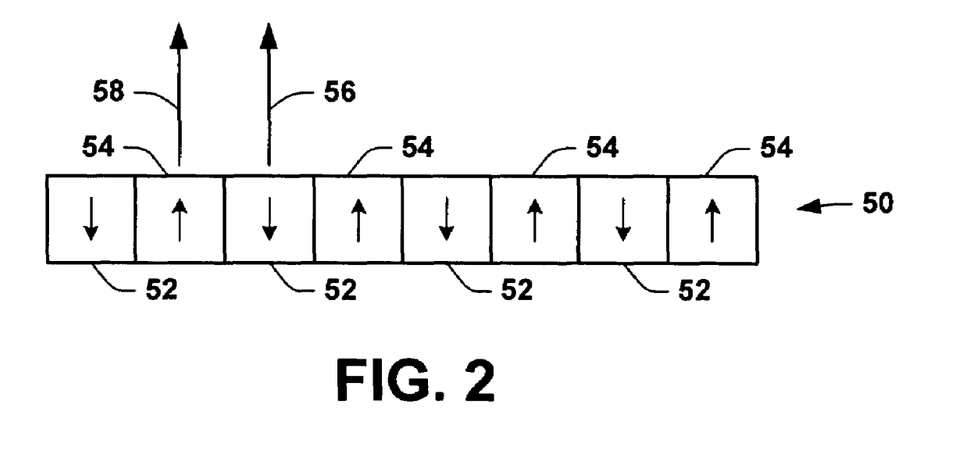
FIG. 2 depicts a schematic example of part of an orientation-patterned material having alternating domains with different non-linear susceptibility that can be analyzed in accordance with an aspect of the present invention.

By way of further example, FIG. 2 is a conceptual drawing of a plurality of adjacent domains in an orientation-patterned material 50. This and other examples described herein use the following coordinate systems, taken from the perspective of the system 10 as shown in FIG. 1, which is defined by x=[100], y=[010], and z=[001] and x'=[110], y'=[1-10], and z'=[001]. In FIG. 2, for example, a first set of domains 52 can be orientated along the [110] direction, and the other set of domains 52 along the [1-10] direction. In the conceptual drawing of FIG. 2, the scattered light 56 corresponds to scattering from the domain 52 having the polarization of [110] and scattered light 58 corresponds to scattered light from the domain 54 having the inverse orientation [1-10]. The arrows in the respective boxes of the domains 52 and 54 denote signs of the second order susceptibility $\chi^{(2)}$ of the orientation-patterned material 50.

Figure 3:
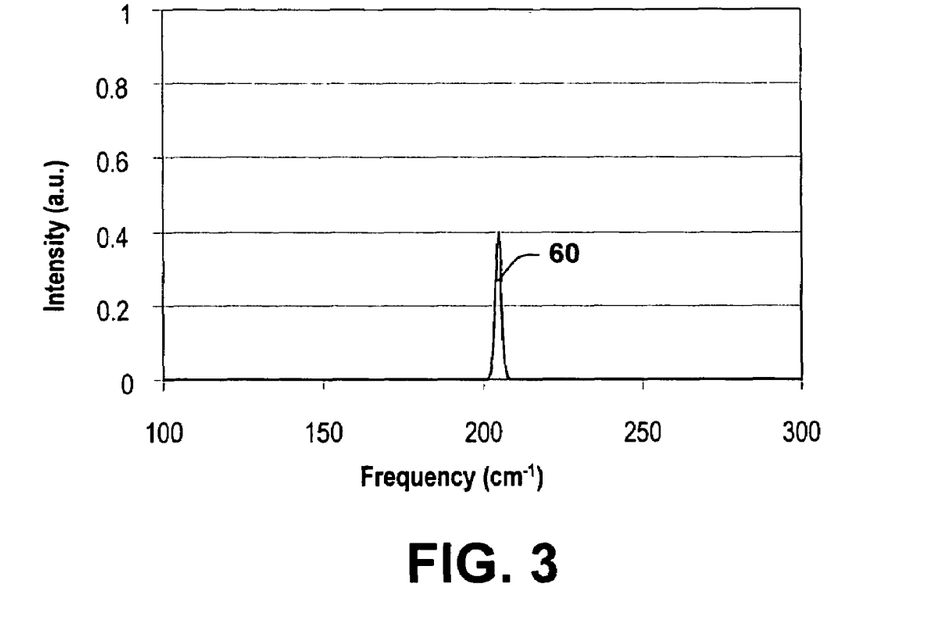
FIG. 3 is a graph depicting the phonon spectrum for scattering off a first domain of the patterned material of FIG. 2.
Figure 4:
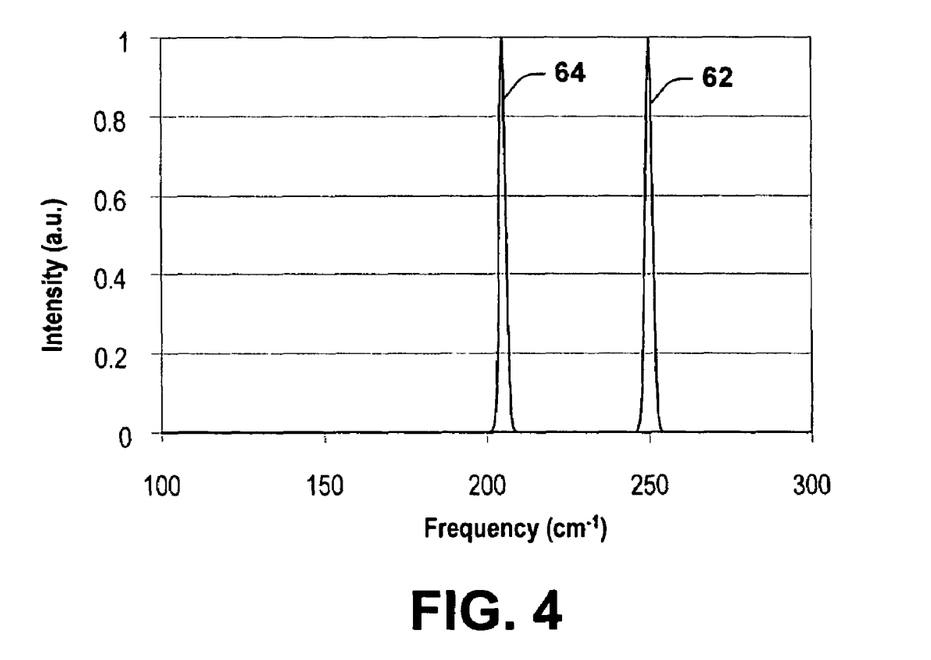
FIG. 4 is a graph depicting the phonon spectrum for scattering off a second domain of the patterned material of FIG. 2.

As a conceptual example (with phonon frequencies appropriate to ZnSe), scattering off the domain 54 corresponding to scattered light 58 gives rise to a TO mode at 205 cm$^{-1}$, and a negligibly small or zero level of LO phonon intensity at a frequency of 250 cm$^{-1}$, as depicted in FIG. 3. For the same polarization configuration, scattering off the inverted domain 52 results in a clearly observable LO phonon at 250 cm$^{-1}$, as well as a change in intensity of the TO mode, as shown in FIG. 4. These intensity changes can arise from symmetry-breaking effects, as discussed below.

In view of the foregoing discussion of the FIGS. 1-4 relating to determining pattern characteristics of orientation-patterned materials, the following discussion expands on the underlying technology. The following also describes how the approach can utilize existing symmetry-breaking effects in the material to enhance the underlying technology. The following discussion employs the Porto notation to denote both the directions of incident beam 16 and scattered beam 24, as well as the incident and scattered polarization directions. For example, z(x,y)-z denotes backscattering along the z-axis with the incident and scattered polarizations along x and y, respectively.

The output intensity of the scattered beam 24 is proportional to $|\hat{e}_i \cdot R_j \cdot \hat{e}_s|^2$, where $R_j$ is the Raman tensor for a phonon propagating along the j direction (where j=x, y, or z), and $\hat{e}_i$ and $\hat{e}_s$ are the unit polarization vectors of the incident and scattered light, respectively. Referred to the principal axes, for example, the deformation potential Raman tensor for zincblende symmetry is represented by:

$$R_A(x) = \begin{pmatrix} 0 & 0 & 0 \\ 0 & 0 & a \\ 0 & a & 0 \end{pmatrix}, R_A(y) = \begin{pmatrix} 0 & 0 & a \\ 0 & 0 & 0 \\ a & 0 & 0 \end{pmatrix},$$

$$R_A(z) = \begin{pmatrix} 0 & a & 0 \\ a & 0 & 0 \\ 0 & 0 & 0 \end{pmatrix},$$

Eq. 1 where the subscript A denotes allowed interactions for an ideal crystal, and the coordinate in parenthesis corresponds to the phonon propagation direction.

By way of continued example, Table 1 shows the expected Raman intensities for backscattering from the (001) and (110) surfaces of a zincblende crystal for various scattering geometries (provided in the Porto notation). Assuming that symmetry-breaking effects are ignored, such as crystal misorientation and electric field effects, the phonon selection rules dictate that one cannot distinguish [110] from [1-10] in either (001) or (110) backscattering upon scanning across adjacent domains. For instance, the configuration z'(x'x')z' is expected to give exactly the same results for both LO and TO phonons as z'(y'y')z', as denoted by $I_3$.

TABLE 1

Deformation Potential

| Intensity Label | Scattering Geometry $k_i(e_i e_s)k_s$ | LO Phonon Selection Rule | TO Phonon Selection Rule |
|---|---|---|---|
| $I_1$ | z(x, x) − z; z(y, y) − z | 0 | 0 |
| $I_2$ | z(x, y) − z; z(y, x) − z | $|d|^2$ | 0 |
| $I_3$ | z'(x', x') − z'; z'(y', y') − z' | $|d|^2$ | 0 |
| $I_4$ | z'(x', y') − z'; z'(y', x') − z' | 0 | 0 |
| $I_5$ | x'(z', z') − x'; x'(y', y') − x | 0 | $|d|^2$ |
| $I_6$ | x'(y', z') − x'; x'(z', y') − x | 0 | $|d|^2$ |

In practice, the broken symmetries that exist in real crystals and other materials can be utilized to help distinguish inverted domains from one another to determine patterning of such materials. As mentioned above, the symmetry-breaking effects can include substrate misorientation, Fröhlic interaction, surface field induced scattering, and second order scattering. Each of these and other symmetry-breaking effects has an associated Raman tensor that can be utilized in conjunction with corresponding phonon selection rules to characterize expected phonon intensities, based on which patterning can be determined.

In discussing each of these symmetry-breaking effects, reference will be made back to the example system of FIG. 1. Additionally, for simplicity of explanation, the phonon selection rules and Raman tensors described with respect to the various symmetry-breaking effects are described in the context of an orientation-patterned zincblende crystal. It will be understood and appreciated that similar Raman tensors and phonon selection rules can be provided for various other types of materials (e.g., other films, waveguides, bulk crystals etc.) based on the teachings contained herein.

Substrate Misorientation

Many orientation-patterned devices are built on substrates that have the (001) plane misoriented toward (1-10) by an angle $\delta$. This misorientation can be leveraged, for example, in generating orientationally inverted epitaxial layers on the substrate. The misorientation leads to a rotation of the crystal (relative to the fixed lab coordinates) described by Euler angles $\alpha=-45°$, $\beta=\delta$, and $\gamma=0$, as embodied by the rotation matrix:

$$A(\alpha, \beta, \delta) = \begin{pmatrix} \frac{\cos\delta}{\sqrt{2}} & \frac{-\cos\delta}{\sqrt{2}} & -\sin\delta \\ \frac{1}{\sqrt{2}} & \frac{1}{\sqrt{2}} & 0 \\ \frac{\sin\delta}{\sqrt{2}} & \frac{-\sin\delta}{\sqrt{2}} & \cos\delta \end{pmatrix}. \quad \text{Eq. 2}$$

The crystal principal axes relative to the lab axes can be transformed from x, y, z to:

$$x'' = \begin{pmatrix} \frac{\cos\delta}{\sqrt{2}} \\ \frac{-\cos\delta}{\sqrt{2}} \\ -\sin\delta \end{pmatrix}, \; y'' = \begin{pmatrix} \frac{1}{\sqrt{2}} \\ \frac{1}{\sqrt{2}} \\ 0 \end{pmatrix}, \; z'' = \begin{pmatrix} \frac{\sin\delta}{\sqrt{2}} \\ \frac{-\sin\delta}{\sqrt{2}} \\ \cos\delta \end{pmatrix}, \quad \text{Eq. 3}$$

The Raman tensor for phonon propagation along the new axes is a linear combination of the tensors in Eq. 1 with coefficients corresponding to the directional cosines as set forth in the following Eq. 4:

$$R_A(x'') = \begin{pmatrix} 0 & -\sin\delta & \frac{-\cos\delta}{\sqrt{2}} \\ -\sin\delta & 0 & \frac{\cos\delta}{\sqrt{2}} \\ \frac{-\cos\delta}{\sqrt{2}} & \frac{\cos\delta}{\sqrt{2}} & 0 \end{pmatrix},$$

$$R_A(y'') = \frac{1}{\sqrt{2}} \begin{pmatrix} 0 & 0 & 1 \\ 0 & 0 & 1 \\ 1 & 1 & 0 \end{pmatrix},$$

$$R_A(A) = \begin{pmatrix} 0 & \cos\delta & \frac{-\sin\delta}{\sqrt{2}} \\ \cos\delta & 0 & \frac{\sin\delta}{\sqrt{2}} \\ \frac{-\sin\delta}{\sqrt{2}} & \frac{\sin\delta}{\sqrt{2}} & 0 \end{pmatrix}$$

The overall result for different polarization configurations is shown in Table 2. For example, row pairs $I_7$-$I_8$, $I_{10}$-$I_{11}$, $I_{12}$-$I_{13}$ and $I_{14}$-$I_{15}$ compare the different intensities expected for scattering off orthogonal (110) planes. In each case, either the LO or TO phonon or both should vary in intensity as one scans across the (110) plane of the material 12. The variation in intensity for the respective phonons can be utilized to determine patterning of the material 12 according to the peaks in a frequency domain representation of phonon intensities (see, e.g., FIGS. 3 and 4).

TABLE 2

| | Coordinates: x'' = 1-10 − δ, y'' = 110, z'' = 001 − δ | | |
|---|---|---|---|
| Intensity Label | Scattering Geometry $k_i(e_i e_s)k_s$ | LO Phonon Selection Rule | TO Phonon Selection Rule |
| $I_7$ | z''(x'', x'')z'' | $|d|^2\cos^2\delta(2\sin^2\delta - \cos^2\delta)^2$ | $|d|^2\sin^2\delta$ |
| $I_8$ | z''(y'', y'')z'' | $|d|^2\cos^2\delta$ | $|d|^2\sin^2\delta$ |
| $I_9$ | z''(x'', y'')z'' | 0 | 0 |
| $I_{10}$ | z''(y'', y'') − x'' | $|d|^2\sin^2\delta$ | $|d|^2\cos^2\delta\delta$ |
| $I_{11}$ | y''(x'', x'') − y'' | 0 | $|d|^2\cos^2\delta(5\sin^2\delta - \cos^2\delta)^2$ |
| $I_{12}$ | x''(y'', z'') − y'' | 0 | $|d|^2\cos^2\delta$ |
| $I_{13}$ | y''(x'', z'') − y'' | 0 | $|d|^2(1 + \sin4\delta)$ |
| $I_{14}$ | z''(z'', z'') − x'' | $|d|^2\sin^2\delta(\sin^2\delta - 2\cos^2\delta)^2$ | $|d|^29\cos^2\delta\sin^4\delta$ |
| $I_{15}$ | y''(z'', z'') − y'' | 0 | $|d|^2(\sin^2\delta + \cos\delta\sin\delta)^2$ |

Fröhlic Interaction

Another type of symmetry-breaking effect is associated with the Fröhlic interaction due to electric field modulation by LO phonons. Due to the partially ionic bonding in certain types of materials, such as zincblende crystals, adjacent layers of atoms have a relative charge difference. This charge difference causes a field between adjacent layers, which, as with capacitors, varies with layer separation. The field is modulated in the case of LO phonons. For TO phonons the sheets of charge simply slide with respect to each other without changing their separation. The field leads to a Raman susceptibility gradient in the material that is linear in phonon wavevector q, arising from the small but finite magnitude given by:

$$q = k_s - k_i = 2\pi(1/\lambda_s - 1/\lambda_i), \quad \text{Eq. 5}$$

where $k_s$ and $k_i$ are the scattered and incident wavevectors associated with the scattered and incident wavelengths $\lambda_s$ and $\lambda_i$, respectively.

The Raman tensor associated with this field-induced contribution can be represented by the diagonal matrix with element $a_F$ as follows:

$$R_F = \begin{pmatrix} a_F & 0 & 0 \\ 0 & a_F & 0 \\ 0 & 0 & a_F \end{pmatrix}. \quad \text{Eq. 6}$$

The elements of the tensor of Eq. 6 are to be added to those of the LO deformation potential tensor (Eq. 1) before squaring to calculate the expected Raman intensity of backscattered light 24. The result of this contribution due to Fröhlic interaction is shown in Table 3. Table 3 depicts Raman intensities for (001) and (110) backscattering accounting for the Fröhlic interaction. For example, the intensities $I_{16}$ and $I_{17}$ correspond to a situation of how the Raman intensity should vary as one scans the incident light beam 16, with fixed polarization, across adjacent domains that have orientations inverted with respect to each other.

From Table 3 and the above-discussion, if orientation patterning takes place, then by (001) backscattering, one should be able to detect the patterning by scanning across the domains (in the direction that the nonlinear optical beams would propagate during device operation) with incident and scattered beam polarizations fixed along the y-axis (see FIG. 1). The y-axis corresponds to the axis of the system 10, which axis may correspond to either the [110] or [1-10] crystal axis of one domain or the adjacent inverted domain. Thus, by comparing the intensities $I_{16}$ and $I_{17}$ to each other, the detected modulation in the phonon intensity of the scattered light 24 can be employed to measure the degree of orientation patterning, as well as the grating period of the material 12.

TABLE 3

Frohlic + Deformation Potential

| Intensity Label | Scattering Geometry $k_i(e_i e_s)k_s$ | LO Phonon Selection Rule | TO Phonon Selection Rule |
|---|---|---|---|
| $I_{16}$ | z'(x', x') − z' | $\|a_F + d\|^2$ | 0 |
| $I_{17}$ | z'(y', y') − z' | $\|a_F - d\|^2$ | 0 |
| $I_{18}$ | z'(x', y') − z' | 0 | 0 |
| $I_{19}$ | x'(z', z') − x'; y'(z, z) − y' | $\|a_F\|^2$ | 0 |
| $I_{20}$ | x'(y', z') − x'; y'(x', z) − y' | 0 | $d^2$ |
| $I_{21}$ | x'(y', y') − x'; y'(x', x') − y' | $\|a_F\|^2$ | $d^2$ |

Because this process is linear in q it is dipole forbidden, as opposed to the allowed process of deformation potential. However, the forbidden contribution can interfere with the allowed one, leading to dips or peaks in Raman spectra of cubic crystals when the laser wavelength is in resonance with an electronic transition (i.e., the band gap) of the crystal. This means that by proper choice of wavelength of the incident beam 16, one can detect the orientation patterning of the material 12 upon scanning across the domains. This mechanism enables one to discriminate between [110] and [1-10] in a crystal with a fixed orientation by rotating the polarization direction of the incident beam 16.

Surface Field Induced Scattering

Another symmetry-breaking effect that can be employed to help characterize patterning of orientation-patterned materials is surface field (SF) induced scattering. For example, if the incident beam 16 is at a wavelength near the optical gap of the material 12, the short absorption depth forces scattering to arise primarily from a region near the surface 18 that does not bear the translational symmetry of the entire material 12. The electric fields associated with the LO phonons or with a free carrier concentration confined near the surface 18 induce a gradient to the electronic susceptibility that gives rise to an additional surface field (SF) tensor component of the Raman tensor associated with the material 12. Alternatively, for a given orientation-patterned crystal 22, if the incident beam 16 is confined to a region close to a heteroepitaxial substrate/film interface (e.g., the junction between the orientation-patterned film 22 and substrate 20), a strong electric field is produced via bending of the energy bands of the two different materials. This electric field induces changes in Raman intensity even when the laser photon energy is below the energy gap.

To account for SF effects, the Raman tensor for the material can be modified by adding terms that characterize these symmetry-breaking interactions. As discussed above, the SF Raman tensor components are added to the conventional Raman tensor (deformation potential of Eq. 1) before squaring. For backscattering off (001) the Raman tensor component for the SF effect, referred to the principal axes, can be expressed as follows:

$$R_{SF}(x) = \begin{pmatrix} 0 & 0 & d \\ 0 & 0 & 0 \\ d & 0 & 0 \end{pmatrix}, R_{SF}(y) = \begin{pmatrix} 0 & 0 & 0 \\ 0 & 0 & d \\ 0 & d & 0 \end{pmatrix}, \quad \text{Eq. 7}$$

$$R_{SF}(z) = \begin{pmatrix} c & 0 & 0 \\ 0 & c & 0 \\ 0 & 0 & b \end{pmatrix}$$

where the subscript SF denotes a process forbidden for the q=0, nonresonant case.

The results for this scattering configuration, as well as backscattering in the x' and y' directions, referred to the x', y', z' axes, are given in Table 4. Thus, Table 4 provides Raman selection rules that account for symmetry-breaking effects of surface electric fields and finite phonon wavevectors. Vertically adjacent entries $I_{24}$ and $I_{25}$ can be used to distinguish the domain [110] from the domain [1-10]. From Table 4 and the foregoing discussion, it becomes evident that one can distinguish between domains of orthogonal orientation through a wide variety of backscattering and polarization configurations. For example, according to the phonon selection rules of Table 4, this can be observed either in backscattering from (001)—$I_{24}$ vs. $I_{25}$—from the top of the film, or from (110) planes on the side of the film—$I_{27}$ vs. $I_{28}$, $I_{29}$ vs. $I_{30}$, or $I_{31}$ vs. $I_{32}$.

TABLE 4

| .SF Intensity Label | Scattering Geometry $k_i(e_i e_s)k_s$ | LO Phonon Selection Rule | TO Phonon Selection Rule |
|---|---|---|---|
| $I_{22}$ | z(x, x) −z; z(y, y) −z | $\|b\|^2$ | 0 |
| $I_{23}$ | z(x, y) −z; z(y, x) −z | $\|d\|^2$ | 0 |
| $I_{24}$ | z(x', x') −z | $\|d + b\|^2$ | 0 |
| $I_{25}$ | z(y', y') −z | $\|d − b\|^2$ | 0 |
| $I_{26}$ | z(x', y') −z; z(y', x') −z | 0 | 0 |
| $I_{27}$ | x'(z, z) −x' | $2\|b\|^2$ | 0 |
| $I_{28}$ | y'(z, z) −y' | 0 | $2\|b\|^2$ |
| $I_{29}$ | x'(y', z) −x' | 0 | $\|d\|^2$ |
| $I_{30}$ | y'(x', z) −y' | 0 | $\|d\|^2 + \|c\|^2$ |
| $I_{31}$ | x'(y', y') −x' | $(1/2)\|a + b − 2c\|^2$ | $\|d\|^2$ |
| $I_{32}$ | y'(x', x') −y' | 0 | $\|d\|^2 + (1/2)\|a + b − 2c\|^2$ |

In the case of a domain that is (001) as viewed from above the film, surface orientation of the side (perpendicular to optical beam propagation direction) is (110), whereas it is (1-10) for an inverted (00-1) domain. However, using the top surface for interrogation of domain orientation may not be ideal because of both possible tapering of domains with vertical propagation from the template, and corrugation of the surface that may originate in the lithography/thin film regrowth process of the template fabrication. By probing a cross-section of the film with backscattering along x' and y' instead, one is guaranteed to observe the orientation patterning and mapping it out as a function of distance upward from the template.

Second Order Scattering

Another symmetry-breaking effect that can help distinguish between different domains in an orientation-patterned material relates to second order scattering of either optical or acoustical phonons. The predicted intensities of these second order modes are governed by selection rules that are different from those of first order optical phonons (e.g., as shown in Tables 1-2). The differences arise particularly because phonons spanning the entire Brillouin zone—not just those near the center—may participate in the scattering process. Thus, the scattered light 24 can include second order scattering effects, including transverse acoustic (TA) phonons and/or longitudinal acoustic (LA) phonons. For acoustical phonons, the predicted intensities are dictated by Brillouin tensors and the elasto-optical coefficients for the material. Because acoustic phonons have much lower energies, the detection system 26 can include a multipass Fabry-Perot interferometer (or other etalon device) to pick out the inelastic scattering from the Rayleigh-broadened excitation laser line. The Fabry-Perot interferometer can provide a transmission spectrum as a function of wavelength due to Brillouin scattering. The Fabry-Perot interferometer can be used in the detection system 26 in place of or in addition to a grating spectrometer. However, the frequencies of second order acoustic modes are often far enough away from the laser line to allow detection with a small grating spectrometer and narrow line holographic filter.

In view of the foregoing discussion, it will be appreciated that the ability to identify and distinguish reversed domains in an orientation patterned material is not limited to first order optical phonons (LO and TO phonons). It is possible that combination modes of both optical and acoustical phonons as well as third order (or higher) modes may be even more sensitive to the engineered changes in orientation of the material 12.

Figure 5:
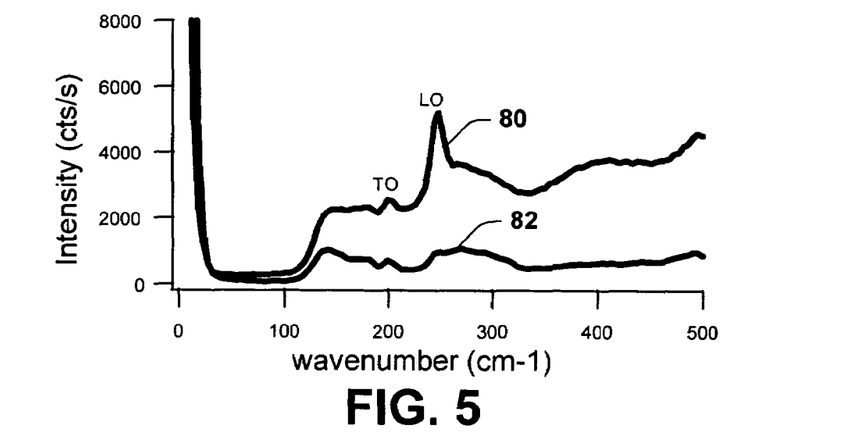
FIG. 5 is a graph of Raman spectra for a first polarization configuration that can be provided according to an aspect of the present invention.
Figure 6:
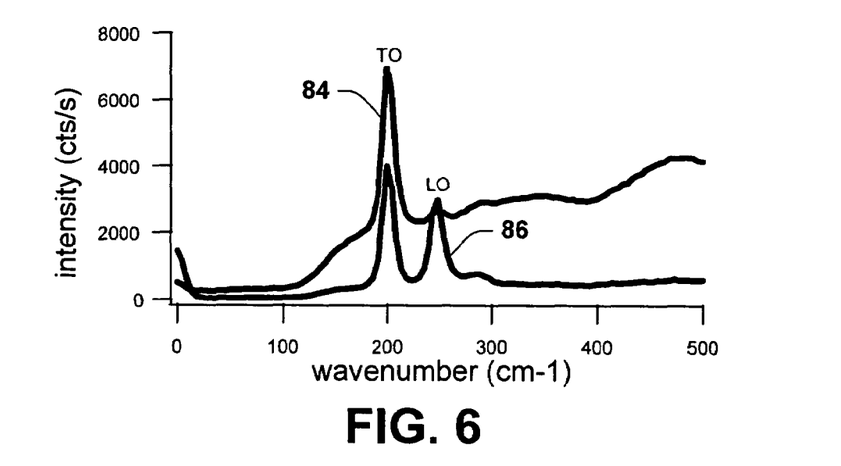
FIG. 6 is a graph of Raman spectra for a second polarization configuration that can be provided according to an aspect of the present invention.
Figure 7:
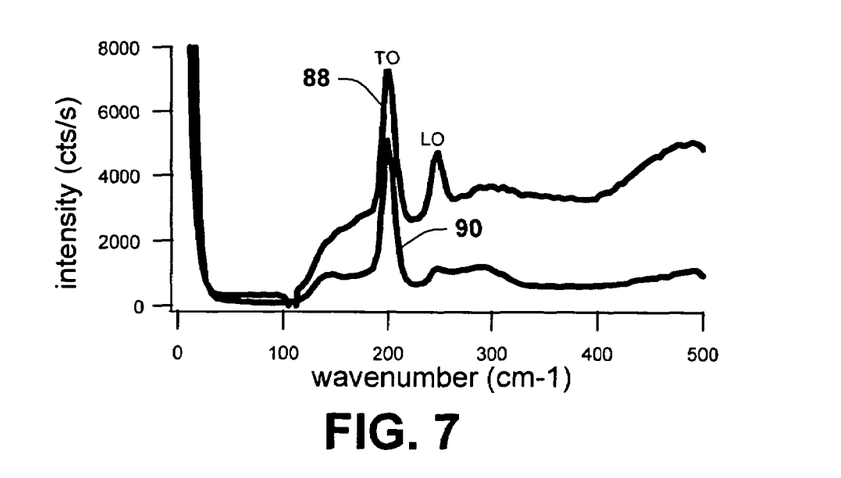
FIG. 7 is a graph of Raman spectra for a third polarization configuration that can be provided according to an aspect of the present invention.

FIGS. 5, 6 and 7 show backscattering data from two surfaces (e.g., the (110) and the (0-10) planes) of a ZnSe (zincblende) crystal for three different polarization configurations. For example, FIG. 5 depicts the Raman spectrum 80 for x'(z'z')x' and a Raman spectrum 82 for y'(z'z')y'. The spectrum 80 exhibits a prominent LO intensity around 250 cm$^{-1}$. FIGS. 6 and 7 depict Raman spectra for the same surface, but for different polarizations of the incident laser beam. In particular, FIG. 6 depicts a spectrum 84 for x'(z'y')x' and a spectrum 86 for y'(z'x')y'. FIG. 7 depicts additional spectra; namely, spectrum 88 for x'(y'y')x', and spectrum 90 for y'(x'x')y'. From FIGS. 5, 6 and 7, it is shown that for each polarization set, there exists a clear distinction in both the LO and TO intensities for the two different faces consistent with the phonon selection rules, again showing the promise of this method for inspecting orientation-patterned materials.

Figure 8:
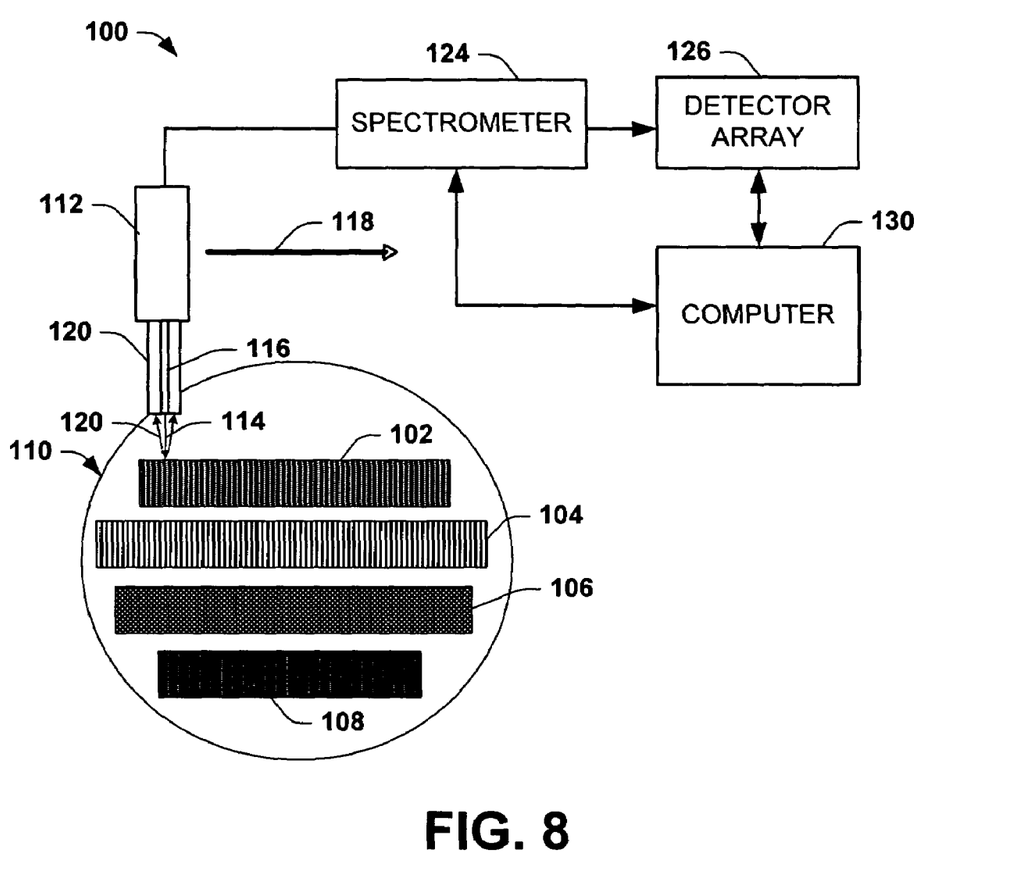
FIG. 8 is an example of another system that can be utilized to ascertain an indication of orientation patterning of non-linear materials in accordance with an aspect of the present invention.

FIG. 8 depicts another embodiment of a system 100 that can be employed to determine patterning of orientation-patterned materials. In the example of FIG. 8, the approach is adapted to a manufacturing inspection process in which the material comprises one or more patterned devices 102, 104, 106 and 108 formed on a wafer 110. For example, the devices 102, 104, 106 and 108 can be single crystal structures grown (e.g., by molecular beam epitaxy or metalorganic chemical or physical vapor deposition processes) on the substrate of the wafer 110.

The system 100 includes a light source 112 that provides an incident beam 114. For example, the light source 112 can be a laser that provides the incident beam 114 at a predetermined frequency (or wavelength) that is in resonance with an electrical transition of the device 102, 104,106 and 108 being scanned. The incident beam is also provided with a known polarization, which can be fixed or can vary, for each of the devices 102, 104, 106 and 108 being scanned. The light source 112 can deliver the incident beam 114 via an optical fiber 116, for example. The beam width at the surface of the devices 102, 104, 106 and 108 should be less than the domain width. To mitigate corrugation effects that result from device processing involving etch-back techniques, for example, the top (001) surface can be polished prior to inspection of devices 102, 104, 106 and 108. The system also allows the polarization of the detected light to be varied in an arbitrary direction.

In the example embodiment of FIG. 8, the light source 112 can be arranged to move relative to a stage on which the wafer 110 is positioned so that the incident beam can scan across the surface of the wafer. For instance, the beam 114 scans across the device 102 in a linear direction 118 that is substantially transverse to the direction of the patterning of the device. In this way, the incident beam 114 can impinge on domains having different orientations. Additionally or alternatively, the stage can also be moved within the wafer 110 plane, but in the perpendicular direction to cause the incident beam to scan across each of the devices 102, 104, 106 and 108, and therefore generate a surface map of their orientation patterning.

A fiber bundle 120, such as may be concentric with the laser fiber 116, can be employed to collect the scattered light and to relay the scattered beam 122 to a scanning spectrometer 124. Additional optical couplings and filters can be in the path between the spectrometer 124 and the fiber bundle 120 that receives the scattered beam 122. For example, the spectrometer grating can be set to a position coincident with the LO phonon so that as the excitation beam moves across the devices, the detected light due to this particular phonon is modulated by the orientation patterning. The spectrometer 124 provides a light spectrum to a detector 126, such as can be implemented as a photo-multiplier tube (PMT).

A computer 130 collects the output of the detector 126 versus scan time and is digitized so that a power spectral density (PSD) can be calculated versus frequency (e.g., using a fast-Fourier transform). The power spectral density (PSD) describes how the power of the received backscattered signal is distributed as a function of frequency. The data from the detector 126 thus provides a 2-D map of the orientation patterning along with the spatial frequency. The computer 130 can provide one or more indications of patterning for each of the devices 102, 104, 106 and 108. As described herein, the resulting PSD curve thus exhibits a peak at the frequency corresponding to the grating period. The computer 130 can also be programmed to determine other characteristics of the orientation patterning, such as the expected crystal orientation expected has been achieved as well as that an expected domain width and/or uniform domain width has been achieved for each device. To determine the indication of patterning, the computer 130 can utilize predetermined Raman tensors for the materials used to form each of the devices as well as phonon selection rules according to the expected orientation, such as described herein.

In view of the foregoing, it becomes evident that the approach described herein can provide a nondestructive method that enables the use of laser spot sizes that can be made smaller than the required domain widths. Polarized Raman also is structurally specific, allowing unambiguous verification of orientation unique to the crystal symmetry. One can enhance the sensitivity of this technique to detection of crystal rotation by choosing the laser wavelength to be in resonance with an electronic transition of the material.

What has been described above includes exemplary implementations of the present invention. It is, of course, not possible to describe every conceivable combination of components or methodologies for purposes of describing the present invention, but one of ordinary skill in the art will recognize that many further combinations and permutations of the present invention are possible. For example, other optical spectroscopies, such as polarized reflectance anisotropy, infrared absorption, or photoluminescence (PL), that are sensitive to crystal symmetry, can also be used for orientation pattern verification. In each case, the incident and scattered light polarizations are held fixed in a given measurement while the sample is scanned with respect to the collection optics. Accordingly, the present invention is intended to embrace all such alterations, modifications and variations that fall within the spirit and scope of the appended claims. In the claims, unless otherwise indicated, the article "a" is to refer to "one or more than one".

What is claimed is:

1. A method to determine at least one characteristic of a material having a spatially modulated nonlinear susceptibility, comprising:
   measuring scattered light in response to an incident beam provided to at least one surface of the material; and
   determining an indication of patterning of the material based on the measured scattered light.

2. The method of claim 1, further comprising:
   scanning the incident beam across at least two adjacent domains of the material to provide the scattered light; and
   discriminating between the at least two adjacent domains based on a modulation of intensity for at least one type of phonon in the scattered light.

3. The method of claim 2, further comprising providing predetermined selection rules according to a type of the material,
   wherein the determination of the patterning further comprises employing a subset of the predetermined selection rules to facilitate determining the indication of patterning for the at least two adjacent domains.

4. The method of claim 3, wherein the predetermined selection rules are adjusted to characterize at least one known symmetry-breaking effect associated with the material.

5. The method of claim 2, wherein the incident beam has a beam width or spot size at the surface of the material that is less than a width of each of the at least two adjacent domains.

6. The method of claim 1, wherein the indication of patterning is determined by calculating a frequency at which at least one type of phonon modulates in intensity based on the scattered light.

7. The method of claim 6, wherein the at least one type of phonon comprises at least one of a longitudinal optical phonon, a transverse optical phonon, a longitudinal acoustic phonon, and a transverse acoustic phonon.

8. The method of claim 1, further comprising providing the incident beam as a linearly polarized beam having a predetermined polarization.

9. The method of claim 1, further comprising performing a fast-Fourier transform to convert a time domain representation of the measured scattered light into a frequency domain representation, such that peaks in intensity of the frequency domain representation correspond to a frequency associated with at least one type of phonon that defines the indication of patterning.

10. The method of claim 1, wherein the input beam has a frequency that is in resonance with an electronic transition of the material.

11. The method of claim 1, wherein the material comprises a crystal film grown on a substrate, the method further comprising scanning the incident beam across a plurality of domains of the material to provide the scattered light.

12. A system to determine a characteristic of a nonlinear crystalline material, comprising:
    means for determining a modulation in intensity of phonons in scattered light from the material; and
    means for determining an indication of patterning of the material based on the determined modulation in phonon intensity.

13. The system of claim 12, further comprising:
    means for scanning an incident beam across at least two adjacent domains of at least one surface of the material to provide the scattered light from the material.

14. The system of claim 13, wherein the incident beam is provided as a linearly polarized beam having a predetermined polarization.

15. The system of claim 13, wherein the incident beam impinges the material with a beam width or spot size that is less than a width of adjacent domains.

16. The system of claim 13, wherein the input beam has a frequency that is in resonance with an electronic transition of the material.

17. The system of claim 12, wherein the means for determining an indication of patterning employs predetermined phonon selection rules selected according to at least one of a type of the material and an expected orientation of the material.

18. The system of claim 12, wherein the material comprises a crystal film grown on a substrate, the incident beam scanning across the surface of the material to provide the scattered light for a plurality of orientation-patterned domains of the material.

19. A system to analyze a material, comprising:
- a light source that provides an incident beam having a predetermined polarization and a predetermined frequency;
- a detection system configured to detect scattered light from at least two adjacent domains of the material in response to the incident beam impinging on the at least two adjacent domains; and
- a computer programmed to determine an indication of patterning for the material based on detected scattered light.

20. The system of claim 19, wherein the incident beam impinges on the material with a width that is less than a width of adjacent domains, the incident beam also having a frequency that is in resonance with an electronic transition of the material, such that by scanning the incident beam across at least two adjacent domains of the material the scattered light is provided with a modulation in phonon intensity, the computer determining the indication of patterning for the material based on the modulation of phonon intensity.

* * * * *